(12) United States Patent
Plumptre

(10) Patent No.: US 9,199,040 B2
(45) Date of Patent: Dec. 1, 2015

(54) DRUG DELIVERY DEVICE LAST DOSE LOCK-OUT MECHANISM

(75) Inventor: David Plumptre, Worcestershire (GB)

(73) Assignee: Sanofi-Aventis Deutschland GmbH, Frnakfurt am Main (DE)

( * ) Notice: Subject to any disclaimer, the term of this patent is extended or adjusted under 35 U.S.C. 154(b) by 560 days.

(21) Appl. No.: 12/788,658

(22) Filed: May 27, 2010

(65) Prior Publication Data

US 2010/0324494 A1    Dec. 23, 2010

Related U.S. Application Data

(60) Provisional application No. 61/182,822, filed on Jun. 1, 2009.

(30) Foreign Application Priority Data

Jul. 10, 2009    (EP) ..................................... 09009056

(51) Int. Cl.
*A61M 5/00*    (2006.01)
*A61M 5/315*    (2006.01)

(52) U.S. Cl.
CPC ....... *A61M 5/31551* (2013.01); *A61M 5/31541* (2013.01); *A61M 5/31511* (2013.01)

(58) Field of Classification Search
CPC . A61M 5/24; A61M 5/3155; A61M 5/31551; A61M 5/31548; A61M 5/31541; A61M 5/31535; A61M 5/31511; A61M 5/31536
USPC .................. 604/207–211, 218, 223, 224, 226
See application file for complete search history.

(56) References Cited

U.S. PATENT DOCUMENTS 3,302,462 A    2/1967    Pursell
5,308,340 A *  5/1994    Harris ........................... 604/208
(Continued)

FOREIGN PATENT DOCUMENTS

DE    93 01 334 U1    4/1993
DE    197 30 999 C1    12/1998
(Continued)

OTHER PUBLICATIONS

Machine Deisgn, Penton Media, vol. 65, No. 11 (1993) p. 36 "Standard Compression Springs Save Space".

*Primary Examiner* — Kami A Bosworth
*Assistant Examiner* — Bradley G Thomas, Jr.
(74) *Attorney, Agent, or Firm* — McDonnell Boehnen Hulbert & Berghoff LLP

(57) ABSTRACT

A method and system for limiting a maximum dose that may be set in a drug delivery device. A dose setting mechanism, which is operable to be coupled to a medication cartridge, comprises a lock-out mechanism that prevents one from setting a dose greater than the medication in the cartridge. The lock-out mechanism comprises a rotatable shaft. A helical groove having a first pitch is provided along a first portion of the rotatable shaft and a second pitch provided along a second portion of the rotatable shaft. The first pitch is different from the second pitch. A third pitch may be provided on a third portion of the shaft. This third pitch is provided at the end of the second pitch and is preferably different than the second pitch. The lock-out mechanism further comprises a non-rotating member disposed on the helical groove of said shaft. During dose setting, the shaft is rotated relative to the non-rotating member while the non-rotating member traverses along the groove from a proximal end of the shaft towards a distal end of the shaft.

21 Claims, 6 Drawing Sheets

(56) References Cited

U.S. PATENT DOCUMENTS

| | | | |
|---|---|---|---|
| 5,423,752 A | 6/1995 | Haber et al. | |
| 5,514,097 A | 5/1996 | Knauer | |
| 5,584,815 A | 12/1996 | Pawelka et al. | |
| 5,591,136 A | 1/1997 | Gabriel | |
| 5,792,117 A | 8/1998 | Brown | |
| 5,820,602 A | 10/1998 | Kovelman et al. | |
| 6,090,080 A | 7/2000 | Jost et al. | |
| 6,221,046 B1* | 4/2001 | Burroughs et al. | 604/153 |
| 6,482,186 B1* | 11/2002 | Douglas et al. | 604/218 |
| 6,582,404 B1* | 6/2003 | Klitgaard et al. | 604/181 |
| 6,936,032 B1 | 8/2005 | Bush, Jr. et al. | |
| 7,195,616 B2* | 3/2007 | Diller et al. | 604/224 |
| 2004/0127858 A1 | 7/2004 | Bendek et al. | |
| 2004/0162528 A1 | 8/2004 | Horvath et al. | |
| 2004/0186437 A1 | 9/2004 | Frenette et al. | |
| 2004/0210199 A1 | 10/2004 | Atterbury et al. | |
| 2004/0236285 A1 | 11/2004 | Fisher et al. | |
| 2005/0137571 A1 | 6/2005 | Hommann | |
| 2006/0153693 A1 | 7/2006 | Fiechter et al. | |
| 2006/0258988 A1 | 11/2006 | Keitel et al. | |
| 2007/0021718 A1 | 1/2007 | Burren et al. | |
| 2007/0093761 A1* | 4/2007 | Veasey et al. | 604/207 |
| 2008/0027397 A1 | 1/2008 | DeRuntz et al. | |
| 2008/0077095 A1 | 3/2008 | Kirchhofer | |
| 2008/0208123 A1 | 8/2008 | Hommann | |
| 2008/0243087 A1* | 10/2008 | Enggaard et al. | 604/208 |
| 2008/0287883 A1* | 11/2008 | Radmer et al. | 604/211 |
| 2009/0227959 A1 | 9/2009 | Hirschel et al. | |
| 2010/0324528 A1* | 12/2010 | Plumptre et al. | 604/506 |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 92/23973 A1 | 8/1996 |
| WO | 96/39214 A1 | 12/1996 |
| WO | 97/10864 A1 | 3/1997 |
| WO | 99/03520 A1 | 1/1999 |
| WO | 01/19434 A1 | 3/2001 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/021072 A1 | 3/2005 |
| WO | 2005/044346 A2 | 5/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

DRUG DELIVERY DEVICE LAST DOSE LOCK-OUT MECHANISM

FIELD OF THE PRESENT PATENT APPLICATION

The present patent application is generally directed to drug delivery devices. More particularly, the present patent application is generally directed to drug delivery devices, such as pen type drug delivery devices. Such devices provide for self administration of medicinal product from a multi-dose cartridge and permit a user to set the delivery dose. The present application may find application in both resettable (i.e., reusable) and non-resettable (i.e., non-reusable) type drug delivery devices. However, aspects of the invention may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease.

In certain types of medication delivery devices, such as pen type devices, cartridges of medication are used. These cartridges are housed in a cartridge holder or cartridge housing. Such cartridges include a bung or stopper at one end. At the other end of the cartridge, the cartridge comprises a pierceable seal. To dispense a dose of medication from such a cartridge, the medication delivery device has a dose setting mechanism that uses a spindle to move in a distal direction towards the cartridge and to press a distal end of the spindle against the bung. This expels a certain set dose of medication from the cartridge. As medication runs low, a user may attempt to set a dose that exceeds the amount of medication left in the cartridge. In order to insure dose accuracy, it is important that a drug delivery device is designed to not allow a user to dial a dose that is greater than the amount of medication remaining in the cartridge. As some users may apply a large turning force (i.e., a large torque load) when attempting to dial a dose that exceeds the amount of medication left in the cartridge, it is important that the drug delivery device be able to withstand a large force.

There is, therefore, a general need to take these perceived dose accuracy issues into consideration when designing either resettable or non-resettable drug delivery devices, such as pen type drug delivery devices.

SUMMARY

According to an exemplary arrangement, a dose setting mechanism for a drug delivery device is provided. The dose setting mechanism, which is operable to be coupled to a cartridge housing that houses a cartridge of medication comprises a last dose lock-out mechanism. The last dose lock-out mechanism prevents a user of the dose setting mechanism from setting a dose of medication that is greater than the medication in the cartridge. The lock-out mechanism comprises a rotatable shaft. A helical groove having a first pitch is provided along a first portion of the rotatable shaft and a second pitch is provided along a second portion of the rotatable shaft. The first pitch is different from the second pitch.

The lock-out mechanism further comprises a non-rotating member disposed on the helical groove of said shaft. During dose setting, the shaft is rotated relative to the non-rotating member while the non-rotating member traverses along the groove from a proximal end of the shaft towards a distal end of the shaft. The non-rotating member traverses along the groove until a dose greater than the medication remaining in the cartridge is selected and the non-rotating member prevents the shaft from rotating and increasing the dose.

According to another arrangement, a method of limiting a maximum dose that may be set in a drug delivery device is provided. The method includes providing a cartridge of medication in said drug delivery device, providing a rotatable shaft, and providing a helical groove along a surface of the rotatable shaft. The helical groove has a first pitch along a first portion of the rotatable shaft and a second pitch along a second portion, and the first pitch is different from the second pitch. The method further includes disposing a non-rotating member on the helical groove of the shaft, and rotating the shaft during dose setting of said drug delivery device. During the rotation, the shaft is rotated relative to said non-rotating member while said non-rotating member traverses along said groove from a proximal end of said shaft towards a distal end of said shaft. The method further includes selecting a dose greater than the medication remaining in the cartridge and utilizing the non-rotating member to prevent a user from further rotating the shaft and increasing the dose.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
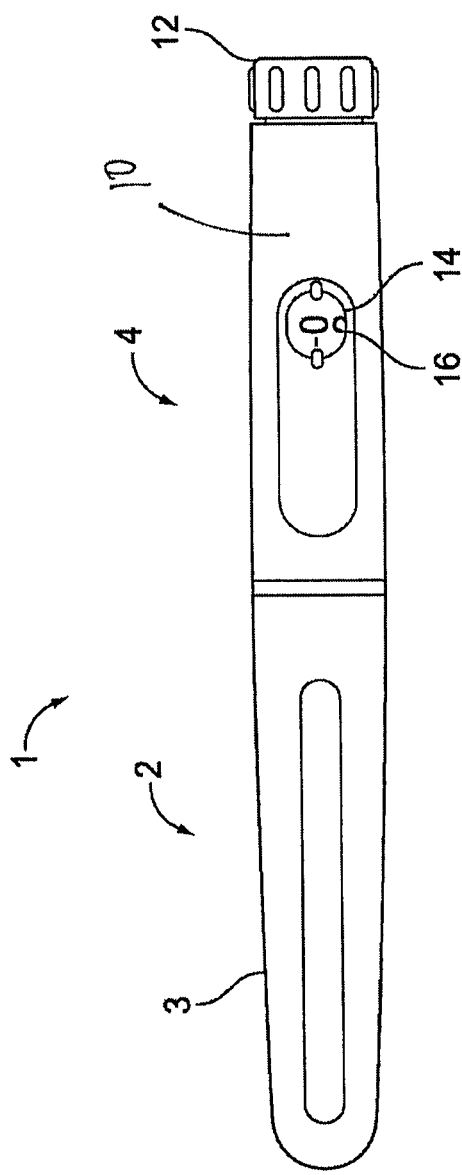
FIG. 1 illustrates an arrangement of the drug delivery device in accordance with the one aspect of the present invention.

Referring to FIG. 1, there is shown a drug delivery device 1 in accordance with an exemplary arrangement. The drug delivery device 1 comprises a housing having a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge housing 2 is secured within the second end of the dose setting mechanism 4. A removable cap 3 is releasably retained over a second end or distal end of a cartridge retaining part or cartridge housing. The dose setting mechanism 4 comprises a dose dial grip 12 and a window or lens 14. A dose scale arrangement 16 is viewable through the window or lens 14. To set a dose of medication contained within the drug delivery device 1, a user rotates the dose dial grip 12 such that a dialed dose will become viewable in the window or lens 14 by way of the dose scale arrangement 16.

Figure 2:
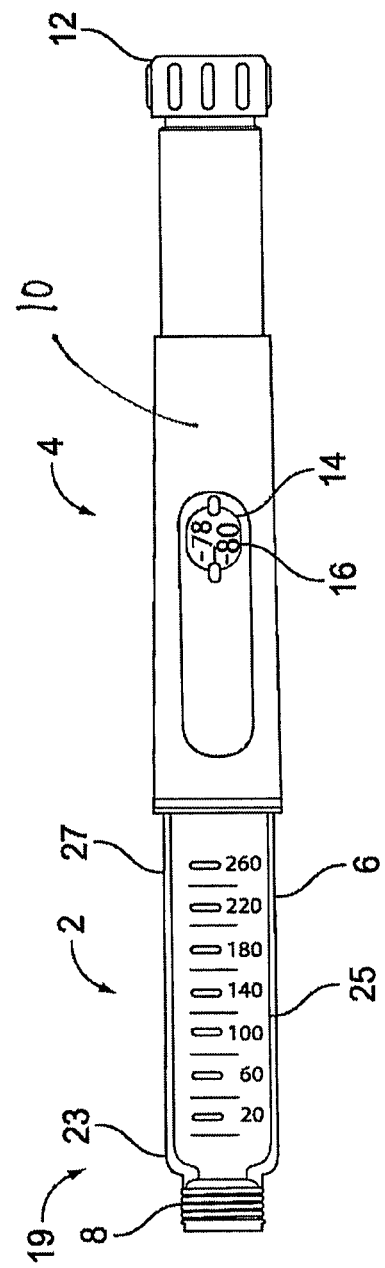
FIG. 2 illustrates the drug delivery device of FIG. 1 with a cap removed and showing a cartridge holder.

FIG. 2 illustrates the medical delivery device 1 of FIG. 1 with the cover 3 removed from a distal end 19 of the medical delivery device 1. This removal exposes the cartridge housing 6. As illustrated, a cartridge 25 from which a number of doses of a medicinal product may be dispensed, is provided in the cartridge housing 6. Preferably, the cartridge 25 contains a type of medicament that can be administered relatively often, such as once or more times a day. One such medicament is either long acting or short acting insulin or an insulin analog. The cartridge 25 comprises a bung or stopper (not illustrated in FIG. 2) that is retained near a second end or a proximal end 33 of the cartridge 25. The medical delivery device also comprises a driver having a spindle (not illustrated in FIG. 2).

The cartridge housing 6 has a distal end 23 and a proximal end 27. Preferably, the cartridge distal end 23 of the cartridge housing 6 comprises a groove 8 for attaching a removable needle assembly. However, other needle assembly connection mechanisms could also be used. If the drug delivery device 1 comprises a resettable device, the cartridge proximal end 27 is removably connected to the dose setting mechanism 4. In one preferred embodiment, cartridge housing proximal end 27 is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 2 may be utilized as a reusable drug delivery device. (i.e., a drug delivery device that can be reset) Where the drug delivery device 1 comprises a reusable drug delivery device, the cartridge 25 is removable from the cartridge housing 6. The cartridge 25 may be removed from the device 1 without destroying the device 1 by merely having the user disconnect the dose setting mechanism 4 from the cartridge housing 6.

In use, once the cap 3 is removed, a user can attach a suitable needle assembly to the groove 8 provided at the distal end 23 of the cartridge housing 6. Such needle assembly may be, for example, screwed onto a distal end 23 of the housing 6 or alternatively may be snapped onto this distal end 23. After use, the replaceable cap 3 may be used to re-cover the cartridge housing 6. Preferably, the outer dimensions of the replaceable cap 3 are similar or identical to the outer dimensions of the dose setting mechanism 4 so as to provide an impression of a unitary whole when the replaceable cap 3 is in position covering the cartridge housing 6 when the device is not in use.

In accordance with an exemplary arrangement, it may be beneficial to limit a maximum dose that may be set in the drug delivery device of FIGS. 1 and 2 when a user attempts to set a dose that is greater than the amount of medication remaining in the cartridge. In order to achieve limiting a maximum dose, the dose setting mechanism 4 of drug delivery device 1 preferably includes a last dose lock-out mechanism. The last dose lock-out mechanism preferably includes a rotatable shaft having a helical groove comprising at least a first and second pitch.

Figure 3:
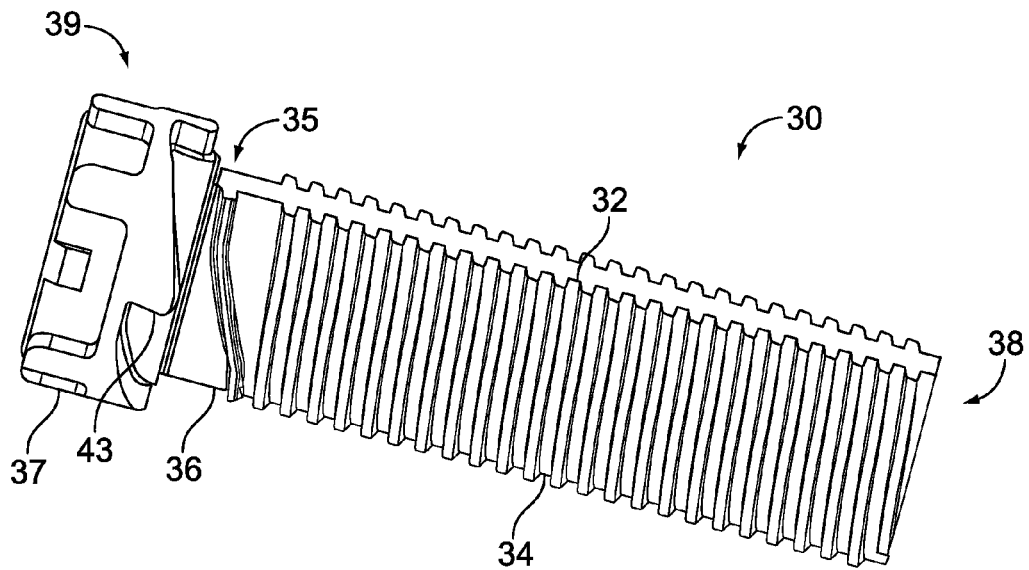
FIG. 3 illustrates a perspective view of a shaft of a dose setting mechanism, such as the dose setting mechanism illustrated in FIG. 2.
Figure 4:
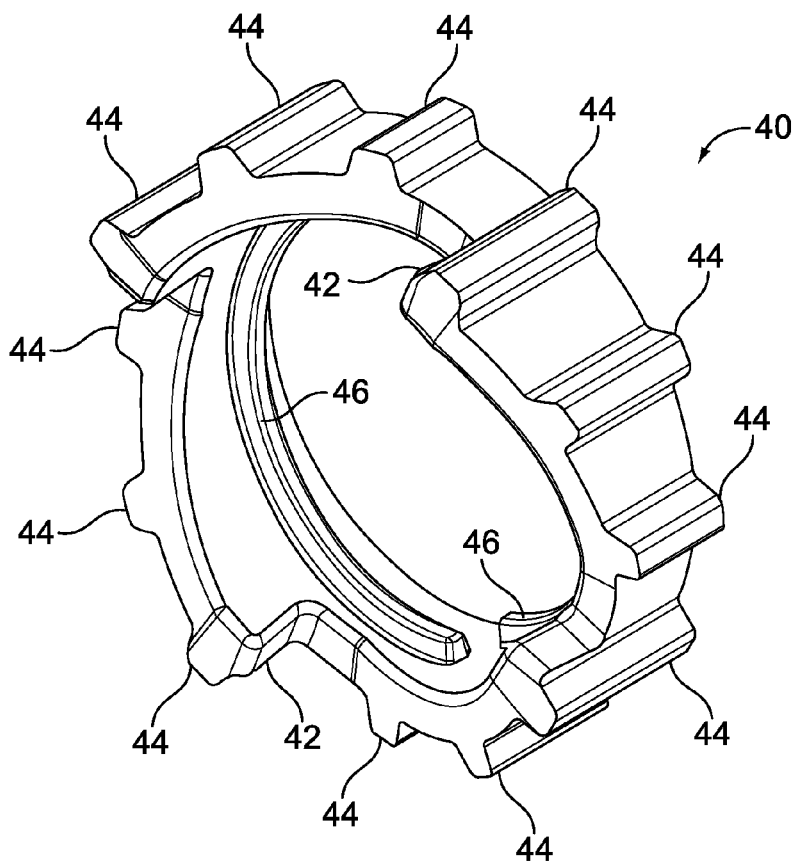
FIG. 4 illustrates a perspective view of a non-rotatable member of a dose setting mechanism, such as the dose setting mechanism illustrated in FIG. 2.

FIGS. 3 and 4 illustrate components of a dose setting mechanism of a drug delivery device, such as the dose setting mechanism 4 of the drug delivery device 1. The dose setting mechanism comprises a last dose lock-out mechanism that prevents a user of the drug delivery device 1 from setting a dose of medication that is greater than the medication remaining in the cartridge of medication. Specifically, FIG. 3 illustrates a rotatable shaft 30 of the last dose lock-out mechanism and FIG. 4 illustrates a non-rotating member 40 of the last dose lock-out mechanism. These two components may be coupled together in the dose setting mechanism, as shown in FIGS. 5-11.

Referring to FIG. 3, the rotatable shaft 30 comprises a helical groove 32 provided along the rotatable shaft 30. The helical groove has a first pitch provided along a first portion 34 of the rotatable shaft 30 and a second pitch provided along a second portion 36 of the rotatable shaft. The first portion is located near a distal end 38 of the rotatable shaft and the second portion is located near a proximal end 39 of the rotatable shaft. Further, the first pitch is different from the second pitch. In an exemplary embodiment, the second pitch is greater than the first pitch, as depicted in FIG. 3. As just one example, the second pitch may be about 2 to about 10 times the width of the first pitch.

In an exemplary embodiment, a third pitch is provided on a third portion 35 of the rotatable shaft. The third pitch is preferably provided at the end of the second pitch and is preferably different than the second pitch. In an exemplary embodiment, the third pitch is less than the second pitch. The third pitch provided along the third portion 35 may be the same or similar to the first pitch provided along the first portion 34 of the rotatable shaft 30. Alternatively, the third pitch provided along the third portion 35 may be different than the first pitch provided along the first portion 34 of the rotatable shaft 30. The third pitch is preferably the same or very similar in width to the first pitch or alternatively the pitch on the non rotating member.

The rotatable shaft also includes a proximal stop mechanism 37 located at the proximal end 39 of the rotatable shaft 30. Preferably, the shape of the proximal stop mechanism 37 is complementary to the non-rotating member 40, which is illustrated in FIG. 4.

The non-rotating member 40 may comprise a nut. For instance, the non-rotating member may be a complete circular nut, as depicted in FIG. 4. However, the non-rotating member could alternatively be a partial nut.

The non-rotating member includes at least one substantially radial stop face 42 The at least one substantially radial stop face 42 is preferably complementary to at least stop face 43 on the proximal stop mechanism 37. In an exemplary embodiment, the non-rotating member comprises a plurality of radial stop faces 42. In embodiments of the dose setting mechanism, the length of the stop face is preferably within a range of about from 0.5 to about 2 mm. However, there is no limit to the length of such stop face as it will generally depend on the design of the device. As such, it may be determined, in part, by certain engineering or design requirements such as an adequate strength for the size of the features based on certain testing parameters, such as Finite Elemental Analysis (FEA).

Further, the non-rotating member comprises a thread form 46 on its interior. Thread form 46 could be a partial thread. In an exemplary embodiment, the thread form 46 comprises two half turns of a two start thread. Other types of thread forms are possible as well. The non-rotating member 40 is capable of being disposed on the helical groove of the rotatable shaft 40, as shown in FIGS. 5-11. The thread form 46 allows the non-rotating member to traverse the helical groove 32 when the rotatable shaft 30 is rotated during dose setting.

The non-rotating member 40 also includes at least one spline feature 44. The spline features 44 may be protrusions from the non-rotating member 40 that may interact with a housing 10 of the drug delivery device 1 that houses the dose setting mechanism 4. The spline feature 44 operates to prevent relative rotation between the non-rotating member 40 and a housing 10 of the drug delivery device that houses the dose setting mechanism 4. In an exemplary embodiment, the non-rotating member comprises a plurality of spline features 44.

Figure 5:
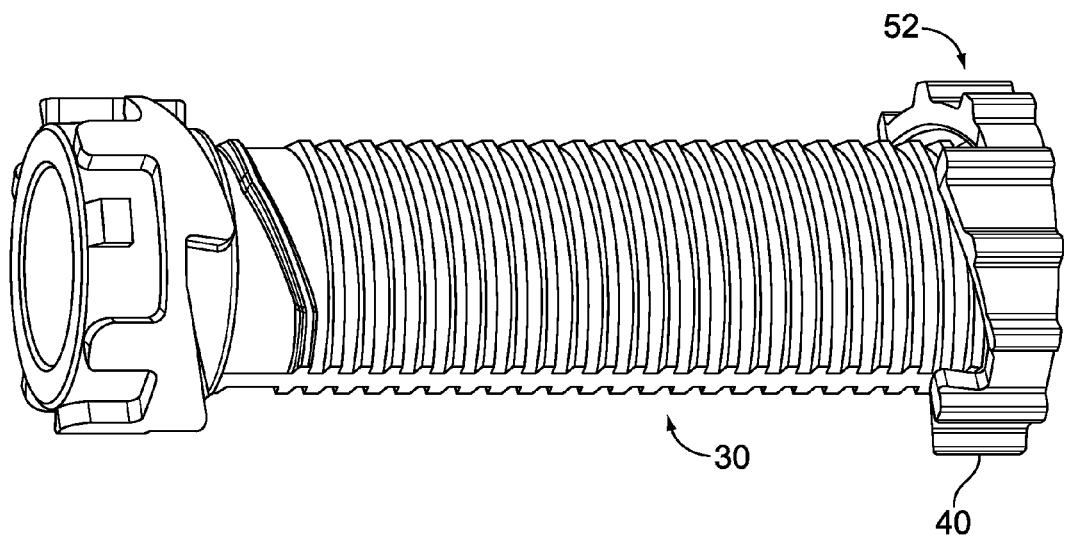
FIG. 5 illustrates a perspective view of the shaft of a dose setting mechanism coupled to a non-rotatable member of a dose setting mechanism, such as the dose setting mechanism illustrated in FIG. 2.
Figure 6:
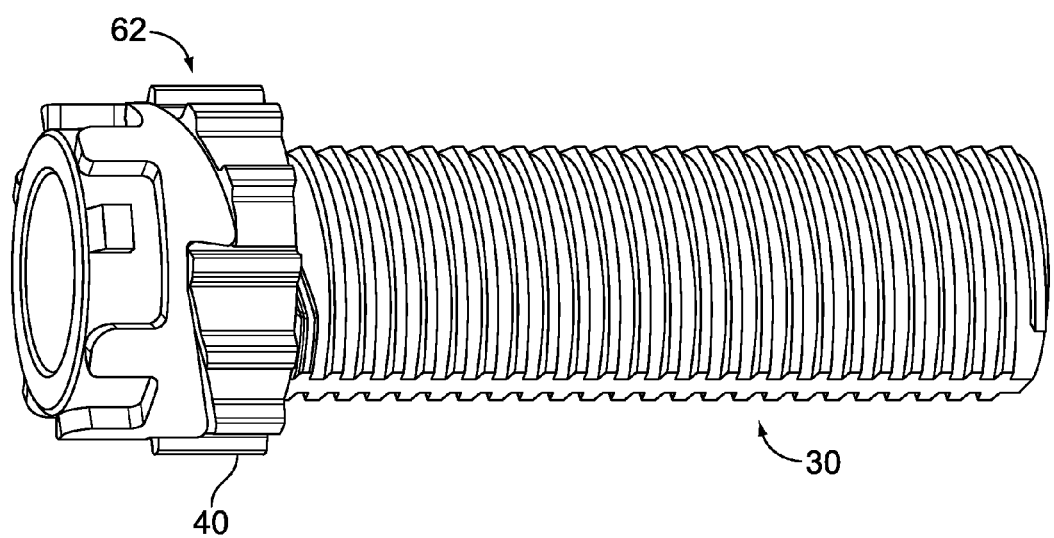
FIG. 6 illustrates a perspective view of the shaft of a dose setting mechanism coupled to a non-rotatable member of a dose setting mechanism, such as the dose setting mechanism illustrated in FIG. 2.

During dose setting of a drug delivery device having a dose setting mechanism with the components illustrated in FIGS. 3 and 4, the shaft 30 is rotated relative to the non-rotating member 40. During rotation, the non-rotating member 40 traverses along the helical groove 32 from the distal end 38 toward the proximal end 39. The non-rotating member traverses along the helical groove 32 until a dose greater than the medication remaining in the cartridge is selected. When a dose greater than the medication remaining in the cartridge is selected, the non-rotating member 40 prevents the shaft from rotating and increasing the dose dialed. Specifically, the stop faces 42 and 43 prevent the shaft from rotating and increasing the dose dialed. As depicted in FIG. 5, the rotatable shaft 30 comprises a distal start position 52. The non-rotating member 40 is located at the distal start position 52 when the drug delivery device cartridge is substantially filled with medication. Further, as depicted in FIG. 6, the rotatable shaft also comprises a proximal stop position 62. The proximal stop position 62 is located at the point the non-rotating member 40 encounters the distal stop mechanism 37. The non-rotating member 40 is located at the distal stop position when the dose dialed equals the amount of medication remaining in the cartridge. A distance between the distal start position 52 and proximal stop position 62 corresponds to an amount of medication contained in the medication cartridge of the drug delivery device. For instance, in the case of a cartridge housing 300 International Units ("units") of medication, there are approximately 300 units of medication when the non-rotating member is located at the distal start position. Further, the non-rotating member is located at the proximal stop position when there are no additional units of medication available. Still further, the non-rotating member is located approximately half-way between (not depicted) the proximal start position 52 and distal stop position 62 when there are approximately 150 units of medication available for dosing.

When the set dose is dispensed from the cartridge, the non-rotating member 40 does not rotate relative to the rotatable shaft 30. Rather, both the non-rotating member 40 and the shaft 30 move in an axial direction.

The operation of the dose setting mechanism will be further described with reference to FIGS. 7-11. For the majority of dose setting, the non-rotating member traverses along the first pitch while traversing along the helical groove 32. However, when the user is setting a dose that is near the limit of the medication remaining in the cartridge, the non-rotating member traverses along the helical groove having a second pitch, which is greater than the first pitch. FIGS. 7-11 illustrate the interaction between rotatable shaft 30 and the non-rotating member 40 during dose setting of the last dose. Specifically, these Figures illustrate the last approximately 90 degrees of rotation of the rotatable shaft. In such an arrangement, the last approximately 90 degrees of rotation may be generally equivalent to about 4 to about 7 units of medicament contained in the cartridge of the injection device. For purposes of clarity, the spline features 44 of the non-rotating member 40 have been omitted. These Figures depict the relative rotation between the non-rotating member 40 and the rotatable shaft 30.

Figure 7:
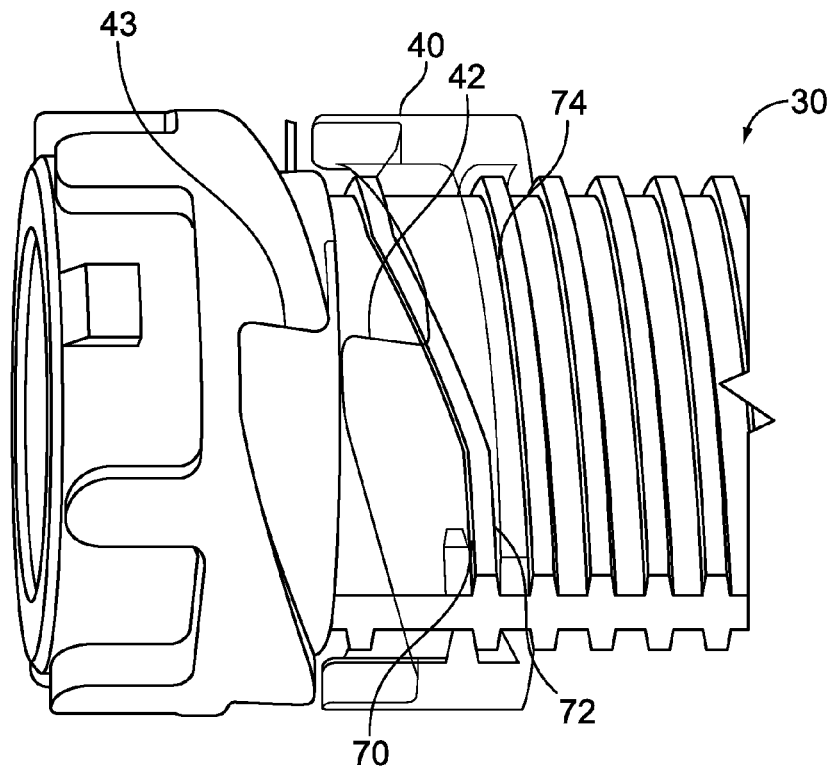
FIG. 7 illustrates a partial perspective view of the shaft of a dose setting mechanism coupled to a non-rotatable member of a dose setting mechanism during dose setting, such as the dose setting mechanism illustrated in FIG. 2.

FIG. 7 depicts the beginning of the last 90 degrees of rotation, where, in this example, the stop feature 42 of the non-rotating member and stop feature 43 of the rotatable shaft 30 just pass each other. At this point, the non-rotating member 40 is traversing along the first pitch and is just about to begin traversing along the second pitch. The threads of the non-rotating member 40 contact the threads of the rotatable shaft 30 at, for example, points 70, 72, and 74.

Figure 8:
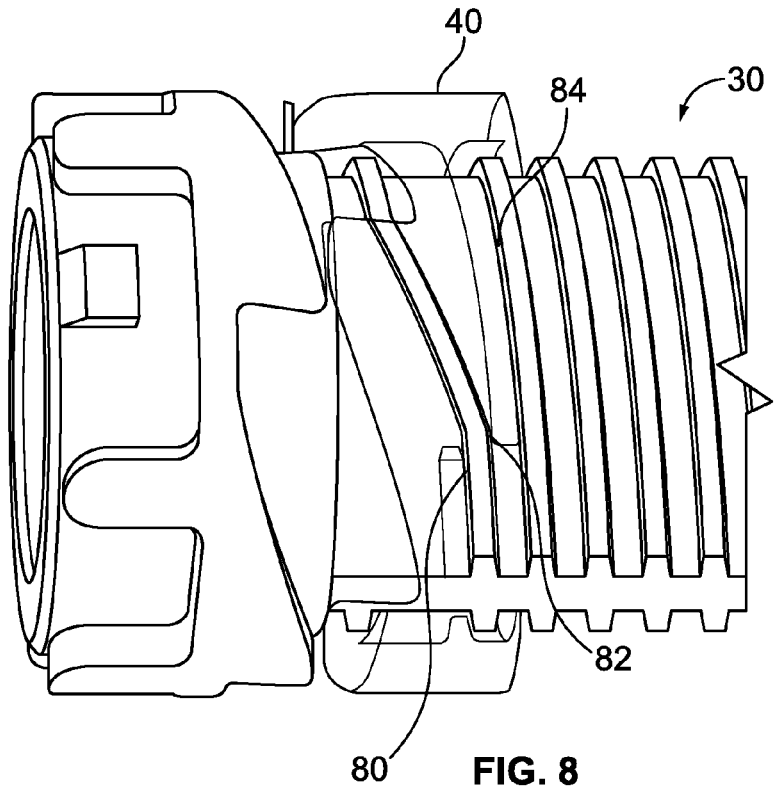
FIG. 8 illustrates a partial perspective view of the shaft of a dose setting mechanism coupled to a non-rotatable member of a dose setting mechanism during dose setting, such as the dose setting mechanism illustrated in FIG. 2.

FIG. 8 depicts when the non-rotating member 40 begins traversing along the second pitch. The threads of the non-rotating member 40 contact the threads of the rotatable shaft 30 at, for example, points 80, 82, and 84. In this example, the second pitch begins at a location corresponding to approximately the last 80 degrees of rotation. However, it should be understood that the second pitch could begin at a different location. For example, the second pitch could begin at a location corresponding to approximately the last 45-360 degrees of rotation. Other locations are possible as well.

Figure 9:
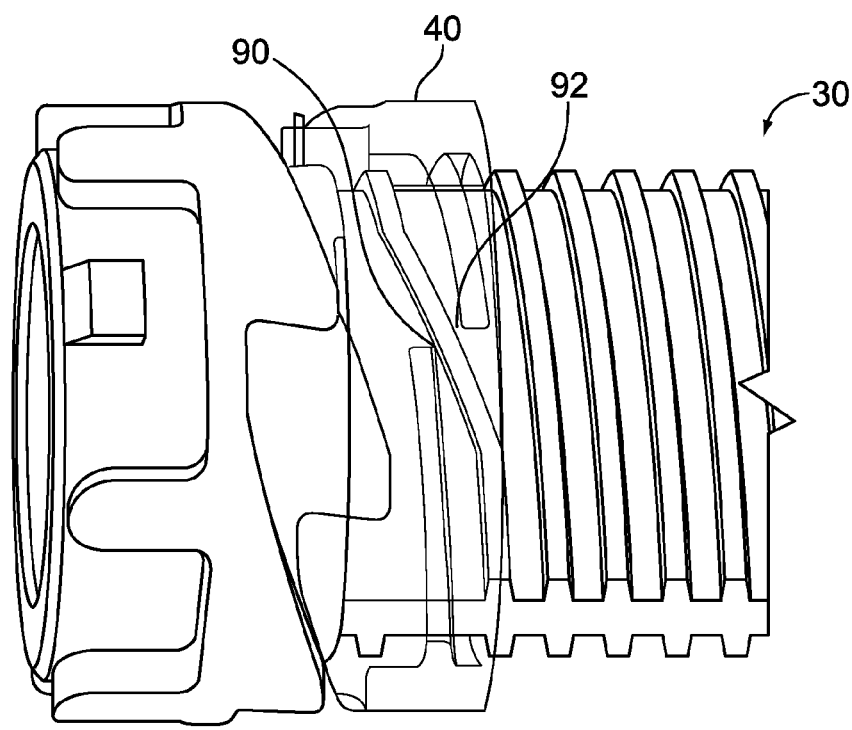
FIG. 9 illustrates a partial perspective view of the shaft of a dose setting mechanism coupled to a non-rotatable member of a dose setting mechanism during dose setting, such as the dose setting mechanism illustrated in FIG. 2.

FIG. 9 depicts when the non-rotating member 40 is approximately midway through traversing along the second pitch. The threads of the non-rotating member 40 contact the threads of the rotatable shaft 30 at points 90 and 92. As FIG. 9 depicts, the nut 40 is adequately guided on both sides due to the twin start threads when it is engaged with the second pitch section. However, the contact area between the threads is minimal. As shown, the twin start threads contact the second pitch area at points 90 and 92. These contact points prevent the non-rotating member 40 from twisting off axis during this increased pitch segment.

Figure 10:
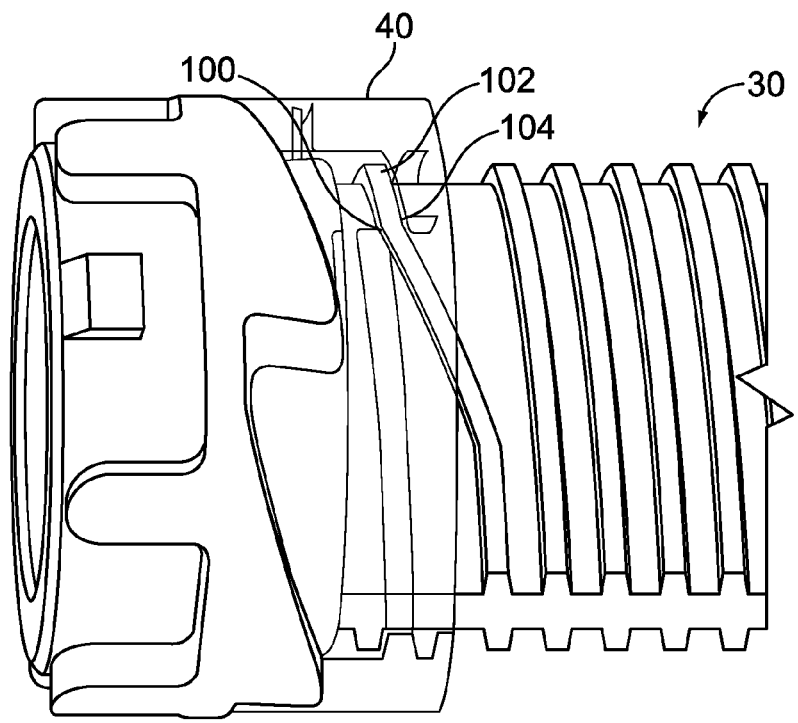
FIG. 10 illustrates a partial perspective view of the shaft of a dose setting mechanism coupled to a non-rotatable member of a dose setting mechanism during dose setting, such as the dose setting mechanism illustrated in FIG. 2.

FIG. 10 depicts when the non-rotating member 40 begins traversing along the third pitch, and also just before the stop feature 42 and stop feature 43 engage. The threads of the non-rotating member 40 contact the threads of the rotatable shaft 30 at, for example, points 100, 102, and 104.

Figure 11:
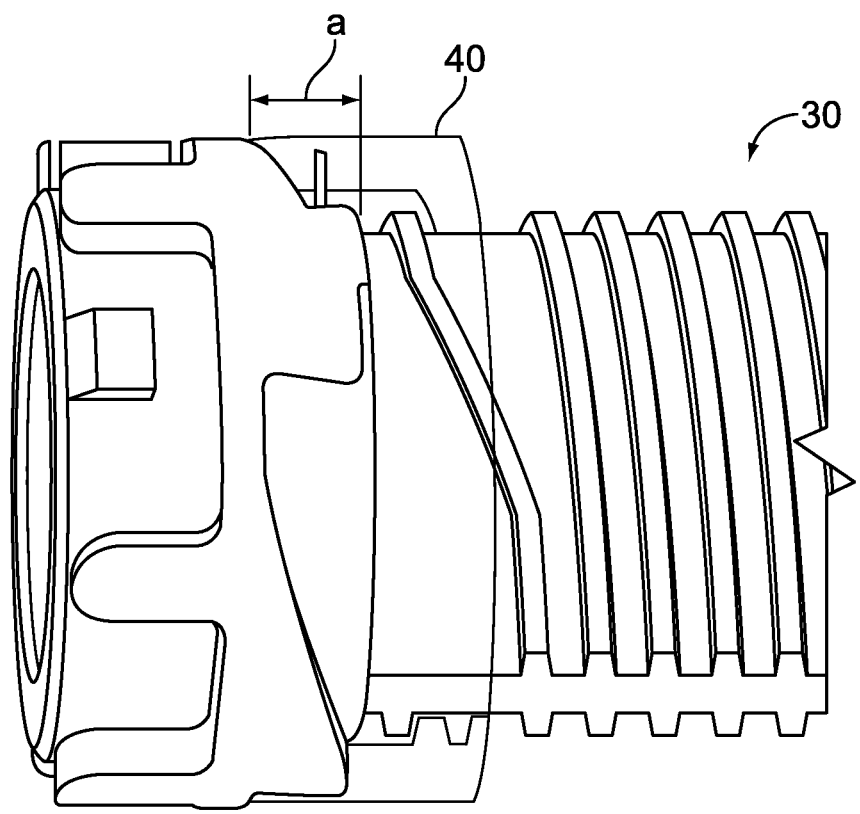
FIG. 11 illustrates a partial perspective view of the shaft of a dose setting mechanism coupled to a non-rotatable member of a dose setting mechanism during dose setting, such as the dose setting mechanism illustrated in FIG. 2.

FIG. 11 depicts when the non-rotating member 40 is finished traversing along the third pitch and when the stop feature 42 and stop feature 43 engage. As FIG. 11 depicts, the stop face 42 of the non-rotating member abuts a complementary stop face 43 of the distal stop mechanism 37 of the rotatable shaft 30. The effective length of the stop faces is shown as the length from A-A. Beneficially, the greater the effective length, the greater the stop force of the last dose lock-out mechanism. By providing the second pitch rather than just a constant pitch on the rotatable shaft, the effective length of the stop faces can be increased. The change of pitch on the rotatable shaft 30 from a first pitch to the increased second pitch allows for an increase in the effective length of the stop faces and therefore creates an increased stop face contact area. The increased stop face contact area increases the stop force when a user attempts to dial a dose greater than the amount of medication remaining in the cartridge.

In addition, the reduced pitch section (i.e., the third pitch on third portion 35) is preferably similar to or identical to the pitch on the nut 40. Therefore, the surface engagement between the threads of the non-rotating member 40 and the threads of the rotatable shaft 30 is increased, thus enabling a higher axial load to be restrained. Because a higher axial load can be restrained due to the increased surface engagement, there is a reduced risk of damage to the threads on these two parts when a high stop torque load is applied by a user. The longer the reduced pitch on third portion 35, the larger the contact surface between the thread forms and therefore the higher the axial load that these thread forms can restrain. It should be understood that the example depicting the last 90 degrees of rotation is for illustrative purposes and is not meant to be limiting. For example, the second pitch could occur at or near the last 180 (i.e., the final one-half turn of the rotatable shaft relative to the non-rotating member.) Still further, the second pitch could occur at or near the last 360 degrees of rotation (i.e., the final complete turn of the rotatable shaft relative to the non-rotating member). Still further, the second pitch could occur at or near the last 540 degrees of rotation (i.e., the final one and a half turns of the rotatable shaft relative to the non-rotating member.) As one of ordinary skill in the art will recognize, other examples are possible as well.

A dose setting mechanism in accordance with an exemplary embodiment increases the stop face area without having a detrimental effect on the stop strength. Accordingly, a dose setting mechanism in accordance with an exemplary embodiment offers an improved last dose lock-out mechanism with an increased stop force. The increased stop force is useful for preventing a user from dialing a dose greater than the remaining medication. As discussed above, the dose setting mechanism described above may be utilized in drug delivery devices that are reusable or in drug delivery devices that are non-reusable.

Exemplary embodiments of the present invention have been described. Those skilled in the art will understand, however, that changes and modifications may be made to these embodiments without departing from the true scope and spirit of the present invention, which is defined by the claims.

I claim:

1. A dose setting mechanism for a drug delivery device, wherein the dose setting mechanism is operable to be coupled to a cartridge housing of the drug delivery device configured to house a cartridge of medication, the dose setting mechanism comprising:
    a last dose lock-out mechanism preventing a user of said dose setting mechanism from setting a dose of said medication that is greater than said medication in said cartridge, said lock-out mechanism comprising:
    a dose setting mechanism housing;
    a rotatable shaft;
    a helical groove having a first pitch provided along a first portion of said rotatable shaft and a second pitch provided along a second portion of said rotatable shaft, said first pitch different from said second pitch; and
    a non-rotating member disposed between said dose setting mechanism housing and said helical groove of said shaft,
    wherein during dose setting of said drug delivery device, said shaft is rotated relative to said non-rotating member and moves axially with respect to said dose setting mechanism housing, while said non-rotating member traverses along said groove from a first end of said shaft towards a second end of said shaft,
    wherein said non-rotating member traverses along said groove until a dose greater than said medication remaining in said cartridge is selected and said non-rotating member prevents said shaft from rotating and increasing said dose, and
    wherein said non-rotating member comprises at least one substantially radial stop face, said at least one substantially radial stop face engaging at least one stop face on said rotatable shaft so that said non-rotating member prevents said shaft from rotating.

2. The invention of claim 1 wherein said rotating shaft comprises a start position and a stop position, wherein a distance between said start position and said stop position corresponds to an amount of medication contained in said cartridge.

3. The invention of claim 1 wherein said second pitch is greater than said first pitch.

4. The invention of claim 1 wherein when said dose is dispensed from said cartridge, said non-rotating member does not rotate relative to said shaft but rather both said non-rotating member and said shaft move in a substantially axial direction.

5. The invention of claim 1 wherein said non-rotating member comprises at least one spline feature, said at least one spline feature preventing relative rotation between said non-rotating member and a housing of said drug delivery device.

6. The invention of claim 1 wherein said non-rotating member comprises a partial thread.

7. The invention of claim 6 wherein said partial thread of said non-rotating member comprises two half turns of a two start thread.

8. The invention of claim 1 wherein said first portion is located near a distal end of said rotatable shaft and said second portion is located near a proximal end of said rotatable shaft.

9. The invention of claim 1
    wherein said non-rotating member comprises a plurality of radial stop faces, said plurality of radial stop faces engaging a plurality of stop faces on said rotatable shaft so that said non-rotating member prevents said shaft from rotating.

10. The invention of claim 1 wherein said drug delivery device comprises a pen type drug delivery device.

11. The invention of claim 10 wherein said pen type drug delivery device comprises a non-reusable pen type drug delivery device.

12. The invention of claim 1 further comprising a third pitch provided along a third portion of said rotatable shaft.

13. The invention of claim 12 wherein said third pitch provided along said third portion of said rotatable shaft is similar to a thread of said non-rotating member.

14. The invention of claim 12 wherein said third pitch provided along said third portion of said rotatable shaft is different from said first pitch provided along said first portion of said rotatable shaft.

15. The invention of claim 12 wherein said third pitch provided along said third portion of said rotatable shaft is different from said second pitch provided along said second portion of said rotatable shaft.

16. The invention of claim 12 wherein said second pitch provided along said second portion of said rotatable shaft is greater than said third pitch provided along said third portion of said rotatable shaft.

17. The invention of claim 12 wherein said first pitch provided along said first portion of said rotatable shaft is generally equal to said third pitch provided along said third portion of said rotatable shaft.

18. The invention of claim 1 wherein said non-rotating member comprises a nut.

19. The invention of claim 18 wherein said nut is a complete circular nut.

20. The invention of claim 1, wherein the second portion begins at a location corresponding to the last 45 to 360 degrees of rotation when the shaft is rotated relative to said non-rotating member.

21. The invention of claim 1 wherein said first end of said shaft comprises a distal end and said second end of said shaft comprises a proximal end.

\* \* \* \* \*